US007589198B2

(12) United States Patent
Tjioe et al.

(10) Patent No.: US 7,589,198 B2
(45) Date of Patent: Sep. 15, 2009

(54) PROCESS FOR THE PREPARATION OF MELAMINE

(75) Inventors: Tjay Tjien Tjioe, Sittard (NL); Eric Grolman, Maastricht (NL); Reinier Franciscus Petrus Grimbergen, Roermond (NL); Michal Kuczynski, Sittard (NL)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 10/522,418

(22) PCT Filed: Jul. 29, 2003

(86) PCT No.: PCT/NL03/00546

§ 371 (c)(1),
(2), (4) Date: Oct. 17, 2005

(87) PCT Pub. No.: WO2004/016599

PCT Pub. Date: Feb. 26, 2004

(65) Prior Publication Data

US 2006/0100428 A1    May 11, 2006

(30) Foreign Application Priority Data

Aug. 15, 2002    (NL)    .................................. 1021287

(51) Int. Cl.
*C07D 251/60*    (2006.01)

(52) U.S. Cl. ...................................... 544/203; 544/201
(58) Field of Classification Search ................. 544/203, 544/201
See application file for complete search history.

(56) References Cited

U.S. PATENT DOCUMENTS 4,408,046 A * 10/1983 Van Hardeveld ............ 544/201
6,355,797 B2    3/2002 Coufal

FOREIGN PATENT DOCUMENTS

WO    99 38852    8/1999

OTHER PUBLICATIONS

International Search Report for PCT/NL2003/000546.

* cited by examiner

*Primary Examiner*—Venkataraman Balasubramanian
(74) *Attorney, Agent, or Firm*—Nixon & Vanderhye P.C.

(57) ABSTRACT

Process for the preparation of melamine, comprising a first mixing step in which at least two melamine-containing flows, originating from at least two different processes for the preparation of melamine, are brought into contact with each other, with a mixture being formed. In one embodiment, at least one melamine-containing flow contains melamine from a low-pressure gas-phase process for the preparation of melamine and at least one melamine-containing flow contains melamine from a high-pressure liquid-phase process for the preparation of melamine.

19 Claims, No Drawings

PROCESS FOR THE PREPARATION OF MELAMINE

CROSS REFERENCE TO RELATED APPLICATION

This application is the National Phase of International Application PCT/NL2003/000546, filed Jul. 29, 2003, which designated the U.S., was published in the English language, and is incorporated by reference herein.

The invention relates to a process for the preparation of melamine.

Such a process is known under the name Stamicarbon Process from 'Melamine and Guanamines', section 4.1.3 of Ullmann's Encyclopaedia of Industrial Chemistry, Sixth Edition, 2001. In the known process gaseous melamine is prepared from urea in a reactor with the aid of a catalyst. The gaseous melamine-containing reaction mixture is cooled with a liquid aqueous phase, with a slurry being formed. In a series of follow-up steps pure melamine is finally separated in the form of crystals with a certain particle size distribution, shape and bulk density.

Another example of a known process for the preparation of melamine is the Melamine Chemicals Process, as shown in section 4.2.1 of the above-mentioned reference. In this known process liquid melamine is prepared from urea at a high pressure (11-15 MPa). The liquid melamine is separated from gaseous by-products and then injected into a cooling unit where cooling takes place with the aid of liquid ammonia. The resulting solid melamine is then isolated as the product.

The known processes have the disadvantage that, with a given process design, it is only to a limited extent possible to influence said properties of the melamine crystals.

It is the object of the invention to reduce said disadvantage.

Said object is achieved in that the process comprises a first mixing step in which at least two melamine-containing flows, originating from at least two different processes for the preparation of melamine, are brought into contact with each other, with a mixture being formed.

The advantage of the process according to the invention is that properties of melamine crystals such as particle size distribution, shape and bulk density can be influenced to a greater extent than is possible in the known process. These properties are amongst other things important in resin preparation using melamine crystals as the feedstock. An example of a resin preparation is the preparation of a melamine-formaldehyde resin, which comprises a dissolving step in which formaldehyde and melamine are dissolved in water. By influencing the properties of the melamine crystals, the dissolving behaviour and thus resin formation can be influenced.

In WO 99/38852 a method of cooling melamine is disclosed, comprising a solidification step in which liquid melamine is mixed with solid melamine. These solidified particles then serve as solid melamine for the solidification of further liquid melamine. Thus, in the solidification step of WO 99/38852 two melamine-containing flows originating from within one process for the preparation of melamine are mixed.

Without having the intention of giving a theoretical explanation of the advantages of the process according to the invention, it is being assumed that differences in the nature and quantity of the impurities in the melamine-containing flows, originating from at least two different processes for the preparation of melamine, can lead to influence being exerted on the physical and/or chemical properties of the final melamine crystals in the process according to the invention. A few examples of impurities are: ammelide, ammeline, cyanuric acid, urea, melam and melem. It is also being assumed that differences in the crystal structure of the melamine in the said melamine-containing flows can lead to influence being exerted on properties. In addition other factors can be of influence.

In the process according to the invention two melamine-containing flows are brought into contact with each other in the first mixing step. A melamine-containing flow is understood to be a flow that contains at least melamine, but in addition may also contain other compounds. Examples of such other compounds are air, nitrogen, $NH_3$, $CO_2$ and $H_2O$. The melamine-containing flow may be gaseous, liquid, solid, or a combination thereof. The melamine-containing flow may consist for example of gaseous or liquid melamine, of a gas mixture of melamine, $NH_3$, $CO_2$ and optionally $H_2O$, of a melamine—ammonia gas/liquid mixture, of melamine dissolved in water, of a slurry of melamine particles in an aqueous phase, or of a powder flow. An aqueous phase is here understood to be a liquid phase which consists substantially of water but in which in addition also other compounds, such as impurities, may be present, in solution or as particles. The at least two melamine-containing flows may be in the same phase, but the may also be in different phases. Examples are: one melamine-containing flow comprises liquid melamine, while a second melamine-containing flow comprises melamine in particle form in an aqueous slurry or dissolved in aqueous solution; one melamine-containing flow comprises liquid melamine, while a second melamine-containing flow is gaseous and comprises melamine in gaseous and/or in particle form; one melamine-containing flow comprises melamine in aqueous solution or slurry, while a second melamine-containing flow is gaseous and comprises melamine in gaseous and/or in particle form. The temperature and the pressure of each of the melamine-containing flows may vary over a large range. If a melamine-containing flow contains gaseous and/or liquid melamine the temperature will usually lie between the melting point of melamine and 450° C., at a pressure between atmospheric and 30 MPa. As is known, the melting point of melamine varies in dependence on factors such as for example the pressure and any ammonia present. If a melamine-containing flow is an aqueous solution or a slurry in an aqueous phase, the temperature will usually lie between 0° C. and 200° C., at a pressure that is at least the autogenous pressure of the flow.

The bringing into contact with each other of the melamine-containing flows in the first mixing step according to the invention can be carried out in many ways, known per se, depending amongst other things on the nature of the melamine-containing flows to be mixed as indicated above. Examples of embodiments of the mixing step are: a vessel or a column, whether or not provided with packing and/or divided into compartments, in which the two flows come together or two tubes which come together at an angle, whether or not with mixing elements.

The at least two melamine-containing flows which are brought into contact with each other in the first mixing step according to the invention originate from at least two different processes for the preparation of melamine. Processes are different when there is a difference in at least one of the process operations needed to obtain the product in question, or at least one difference in the sequence of the process operations.

Examples of differences in a process operation are:

different process conditions such as temperature, pressure, composition, and/or difference in the nature or type of the equipment used.

A difference in temperature is understood to be a temperature difference that is larger than 5° C. and that is also larger than 2% of the lowest temperature expressed in ° C.

A difference in pressure is understood to be:
- a pressure difference that is larger than 20% of the lowest absolute pressure for pressures below 1 MPa absolute, or
- a pressure difference that is larger than 10% of the lowest absolute pressure, for pressures above 2 MPa, or
- a pressure difference that is larger than 0.2 MPa if the lowest pressure lies between 1 MPa and 2 MPa.

A difference in composition is understood to mean that the content of at least one of the components differs by more than 4% in absolute terms.

An example of a difference in the nature or type of the equipment used is for example the use of a packed bed instead of a fluidized bed.

An example of two different processes are: the aforementioned Stamicarbon low-pressure process, and the Melamine Chemicals high-pressure process as described in 'Melamine and Guanamines', sections 4.1.3 and 4.2.1, respectively, of Ullmann's Encyclopaedia of Industrial Chemistry, Sixth Edition, 2001. However, according to the above definition two low-pressure processes such as the Stamicarbon process and the BASF process (section 4.1.1) are also different. It is also possible for two high-pressure processes such as the Melamine Chemicals process and the Nissan process (section 4.2.3) to be different according to the definition given above. Finally, two processes operating on the same basic principle, for example two Stamicarbon processes, may also differ, such as for example when the one process operates at a reactor pressure of 0.5 MPa and the other at 1 MPa.

During the first mixing step according to the invention a mixture is formed. The mixture can then be treated further in a known way to separate the melamine, depending on the nature of the mixture.

In an embodiment of the invention at least one melamine-containing flow contains gaseous and/or liquid melamine and the process according to the invention comprises a cooling step during or after the first mixing step, in which the mixture is cooled to a temperature below 250° C. This yields solid melamine. The solid melamine preferably has a $D_{90}$ between 10 µm and 100 µm, more preferably between 20 µm and 500 µm, most preferably between 25 µm and 350 µm. As is known, '$D_\alpha$ of β µm' means that α wt. % of the particles has a particle size which is at most β µm.

In this embodiment at least one melamine-containing flow contains gaseous and/or liquid melamine, it also being possible for the flow to contain other compounds such as $NH_3$ and $CO_2$; examples of such a flow are: the reactor effluent in a gas-phase process for the preparation of melamine; the liquid reactor effluent in a high-pressure, non-catalytic process for the preparation of melamine; a liquid or gaseous flow of melamine obtained by heating previously prepared melamine powder.

In the cooling step the mixture is cooled to below 250° C. Cooling can be carried out in a way known per se; it is also possible for the melamine in one of the melamine-containing flows to serve as the coolant, for example by feeding it as a powder flow and bringing it into contact with the at least one melamine-containing flow which contains gaseous and/or liquid melamine. Preferably the cooling step is carried out by bringing the mixture into contact with an aqueous phase. This has the advantage that a part of impurities that may be present in the melamine-containing flow will dissolve in the aqueous phase. In an embodiment at least one melamine-containing flow contains water as the continuous phase, and the cooling step is carried out during the mixing step by bringing the at least one melamine-containing flow which contains gaseous and/or liquid melamine into contact with the at least one melamine-containing flow which contains water as the continuous phase. An example of this embodiment is the bringing into contact in a column of a melamine melt from a high-pressure process with gaseous melamine from a low-pressure process, with the cooling step being carried out in the same column by means of an aqueous phase. In another embodiment a melamine-containing aqueous flow from the cooling step of a gas-phase process is used for the cooling step of a melamine melt from a high-pressure process.

Preferably the cooling step is carried out by bringing the mixture into contact with gaseous and/or liquid ammonia. This has the advantage that an anhydrous melamine product can be obtained directly if no water was present in the melamine-containing flows.

Preferably at least one melamine-containing flow contains melamine from a low-pressure gas-phase process for the preparation of melamine, and at least one melamine-containing flow contains melamine from a high-pressure liquid-phase process for the preparation of melamine. This enables use to be made of differences in properties that are present between the melamines. Examples of such properties are chemical composition, colour, crystal structure, particle size and other properties. An example of this preferred embodiment is the spraying of melamine melt from a high-pressure process in a quench vessel which is also fed with a gaseous melamine-containing flow from a low-pressure process and in which liquid ammonia is sprayed as the coolant, with the ammonia completely evaporating.

A further embodiment of the process according to the invention comprises a second mixing step during or after the first mixing step in which the mixture is brought into contact with an aqueous phase, followed by a crystallization step, in which the mixture is cooled by at least 5° C., yielding solid melamine, followed by a separation step, in which the solid melamine is isolated from the mixture. During the second mixing step the mixture is brought into contact with an aqueous phase. An example is the mixing of solid melamine from a high-pressure process with solid melamine from a low-pressure process, with an aqueous phase being added. This has the advantage that a part of the impurities dissolves in the water and as a result will influence the crystallization behaviour of the mixture. The aqueous phase consists substantially of water but may also contain other compounds. Examples of other compounds are melamine, by-products of melamine, ammonia, or compounds used to adapt the pH such as acids or bases. Bringing the mixture into contact with the aqueous phase will result in part of the melamine going into solution. Preferably at least 30 wt. % of the melamine goes into solution, more preferably at least 50 wt. %. The temperature of the mixture is between 50 and 250° C., preferably between 80 and 200° C. The pressure of the mixture lies between the autogenous pressure of the mixture at the corresponding temperature and 20 MPa, preferably between 0.1 MPa and 10 MPa. In an embodiment the overpressure above the autogenous pressure is realized using ammonia. After the mixture has been brought into contact with the aqueous phase, a crystallization step is carried out. In this step the mixture, which in this step is understood to be the original mixture together with the aqueous phase, is cooled by at least 5° C., with the pressure optionally being lowered. Cooling can be carried out with the aid of methods known per se, such as, for example, by means of a heat exchanger or by evaporating a part of the water at reduced pressure. Preferably the mixture is cooled by at least 20° C., more preferably by at least 30° C. As the solubility of melamine in water decreases at a decreasing temperature, cooling of the mixture will result in the formation of solid melamine. The solid melamine that is present in the mixture after the crystallization step, has at least in part been formed during the crystallization step, but can also in part be solid melamine which has not gone into solution. After the crystallization step a separation step is carried out, in which the solid melamine is isolated from the mixture. The separation step can be carried out by means of methods known per se, such as, for example, by means of a centrifuge, band filter, filter disk, or filter candle.

In an embodiment virtually all the melamine is dissolved with the aid of heating and/or addition of an aqueous flow in a dissolving step during or after the second mixing step and prior to the crystallization step. This has the advantage that maximum influence can be exerted on the crystallization by means of the dissolved impurities.

In yet another embodiment of the process according to the invention at least one melamine-containing flow contains water as the continuous phase and the mixture is subjected, after the first mixing step, to a crystallization step in which the mixture is cooled by at least 5° C., with solid melamine being formed, followed by a separation step in which the solid melamine is isolated from the mixture. An example is the mixing of a melamine solution from a gas-phase process with solid melamine from a liquid-phase process.

In this embodiment it can be advantageous to feed another aqueous phase to the mixture during or after the first mixing step, for example if it is desirable to bring a larger part of the melamine in the mixture into solution.

In an embodiment the melamine-containing flow which contains water as the continuous phase contains melamine from a low-pressure gas-phase process and is saturated with melamine to between 70% and 110%. The melamine saturation of an aqueous flow is defined as the melamine concentration in the flow divided by the maximum melamine concentration at thermodynamic equilibrium (at the given process conditions) times 100%. A saturation of more than 100% is thermodynamically unstable, but as is known it can exist for a short time before the shift to 100% saturation is initiated. The advantage of this embodiment is that the properties of the final product are determined on the one hand by the shape and particle size of the non-dissolved melamine crystals and on the other hand by the impurities of the dissolved melamine. By introducing variations in the above parameters a wide range of product characteristics can be created.

Also when the crystallization step is carried out during or after the mixing step, preferably at least one melamine-containing flow contains melamine from a low-pressure gas-phase process for the preparation of melamine and at least one melamine-containing flow contains melamine from a high-pressure liquid-phase process for the preparation of melamine.

In the process according to the invention the mixture is preferably subjected to a purification step after the dissolving step and prior to the crystallization step, this purification step comprising:
- a treatment with $NH_3$ at a pressure between 1 MPa and 20 MPa and a temperature between 100 and 250° C., more preferably at a pressure between 2 MPa and 10 MPa and a temperature between 120 and 200° C., and
- optionally an adsorption and/or filtration step.

The said treatments with $NH_3$, the adsorption step, for example with activated carbon, and the filtration step can be carried out with the aid of a method known per se. The advantage of this embodiment is that the quantity of contaminants that influence the crystallization can be controlled.

Preferably the mixture in the crystallization step is cooled to a temperature between 100° C. and 25° C., more preferably to a temperature between 80° C. and 40° C.

The melamine obtained according to the invention can be used for the preparation of amino-aldehyde resins such as melamine-formaldehyde resin or melamine-urea-formaldehyde resin. The invention therefore also relates to such resins.

The invention is further elucidated by means of a number of examples and a comparative experiment.

EXAMPLE I 2 kg/hour of a melamine-containing flow, which contains water as the continuous phase and which has a temperature of 97° C., contains 4 wt. % dissolved melamine from a Stamicarbon gas-phase process. The said flow is mixed with 0.4 kg/hour of a melamine-containing flow which contains water as the continuous phase, has a temperature of 97° C., originates from a high-pressure liquid-phase process and in which 6 wt. % melamine is present, of which a part as solid material. The mixture is cooled to 60° C. in a crystallizer, upon which more solid melamine is formed. The solid melamine is separated by filtration. The separated solid melamine has a $d_{50}$ of 46 μm and a $d_{90}$ of 98 μm. As is known, the parameters $d_{50}$ and $d_{90}$ are commonly used indicators for particle size and particle size distribution; $d_{50}$ and $d_{90}$ were measured with a laser diffraction technique on the dry powder in air (Sympatec).

EXAMPLE II 2 kg/hour of a melamine-containing flow, which contains water as the continuous phase and which has a temperature of 97° C., contains 4 wt. % dissolved melamine originating from a Stamicarbon gas-phase process. The said flow is mixed with 0.4 kg/hour of a melamine-containing flow which contains water as the continuous phase, has a temperature of 97° C., originates from a high-pressure liquid-phase process and in which 4 wt. % melamine is present. The mixture is cooled to 60° C. in a crystallizer, upon which solid melamine is formed. The solid melamine is separated by filtration. The separated solid melamine has a $d_{50}$ of 42 μm and a $d_{90}$ of 96 μm.

Comparative Experiment 2.4 kg/hour of a melamine-containing flow, which contains water as the continuous phase and which has a temperature of 97° C., contains 4.3 wt. % dissolved melamine originating from a Stamicarbon gas-phase process. The said flow is cooled to 60° C. in a crystallizer, upon which solid melamine is formed. The solid melamine is separated by filtration. The separated solid melamine has a $d_{50}$ of 87 μm and a $d_{90}$ of 183 μm. The melamine has a larger particle size than according to the examples I and II; the melamine from the comparative experiment has a longer dissolution time during resin preparation than the melamine from examples I and II, which is undesirable.

The invention claimed is:

1. Process for the preparation of melamine comprising;
   (a) providing a first melamine-containing flow made from a low-pressure gas-phase process for the preparation of melamine from urea,
   (b) providing a second melamine flow made from a high-pressure liquid-phase process for the preparation of melamine from urea,
   (c) bringing together in a first mixing step the first and second melamine-containing flows to form a mixture thereof, and (d) cooling the mixture in a cooling step to obtain solid particulate melamine having a particle size $D_{90}$ of between 10 μm to 1000 μm.

2. Process according to claim 1, wherein the cooling step (d) is practiced during or after the first mixing step (c), and wherein the mixture is cooled to a temperature below 250° C.

3. Process according to claim 2, wherein the cooling step (d) comprises bringing the mixture into contact with an aqueous phase coolant.

4. Process according to claim 2, wherein at least one of the first and second melamine-containing flows contains water as a continuous phase, and wherein the cooling step (d) is practiced during the first mixing step (c) by mixing the at least one melamine-containing flow which contains water as the continuous phase with at least one other melamine-containing flow.

5. Process according to claim 1, wherein the cooling step (d) is practiced during the first mixing step (c), and wherein the first mixing step (c) comprises bringing the mixture into contact with gaseous and/or liquid ammonia.

6. Process according to claim 1, further comprising a second mixing step (e), during or after the first mixing step (c), wherein the second mixing step (e) comprises bringing the mixture into contact with an aqueous phase coolant, and wherein the cooling step (d) includes a crystallization step (d1) which comprises cooling the mixture by at least 5° C. to form the solid particulate melamine, followed by a separation step (d2) comprising isolating the solid melamine from the mixture.

7. Process according to claim 6, further comprising a dissolving step (f), during or after the second mixing step (e) and prior to the crystallization step (d1), wherein the dissolving step (f) comprises dissolving virtually all the melamine with the aid of heating and/or the addition of an aqueous flow.

8. Process according to claim 1, wherein at least one of the first and second melamine-containing flows contains water as a continuous phase, and wherein the process further comprises, after the first mixing step (c), a crystallization step which comprises cooling the mixture by at least 5° to form solid melamine, followed by a separation step which comprises isolating the solid melamine from the mixture.

9. Process according to claim 8, wherein the at least one melamine-containing flow which contains water as the continuous phase is the first melamine-containing flow originating from the low-pressure gas-phase process for the preparation of melamine from urea and is saturated to between 70% and 110% with melamine.

10. Process according to claim 7, further comprising a purification step (g) after the dissolving step (f) and prior to the crystallization step (e1), and wherein the purification step (g) comprises:

(g1) treating the mixture with $NH_3$ at a pressure between 1 MPa and 20 MPa and a temperature between 100° C. and 250° C., and (g2) optionally conducting an adsorption step and/or a filtration step.

11. Process according to claim 6, comprising cooling the mixture in the crystallization step (d1) to a temperature between 100° and 25° C.

12. Process according to claim 1, wherein steps (c) and (d) are practiced together in a quench vessel, and wherein the process further comprises introducing a liquid ammonia flow as a coolant into the quench vessel.

13. Process according to claim 12, further comprising allowing the ammonia to evaporate from the quench vessel.

14. Process for the preparation of melamine comprising:

(a) providing a melamine-containing gaseous flow made from a low-pressure gas-phase process for the preparation of melamine from urea;

(b) providing a melamine-containing melt flow made from a high-pressure liquid-phase process for the preparation of melamine from urea;

(c) spraying the melamine-containing melt flow into contact with the melamine-containing gaseous flow so as to form a mixture thereof; and (d) cooling the mixture in a cooling step to obtain solid particulate melamine having a particle size $D_{90}$ of between 10 μm to 1000 μm.

15. Process according to claim 14, wherein step (d) comprises spraying liquid ammonia as a coolant into contact with the mixture.

16. Process according to claim 15, wherein steps (c) and (d) are practiced simultaneously within a quench vessel.

17. Process for the preparation of melamine comprising:

(a) providing a first melamine-containing flow made from a low-pressure gas-phase process for the preparation of melamine from urea;

(b) providing a second melamine-containing flow made from a high-pressure liquid-phase process for the preparation of melamine from urea; and (c) bringing the first and second melamine-containing melt flows into contact with one another so as to form a mixture thereof; and (d) simultaneously with step (c), cooling the mixture by using one of the first and second melamine-containing flows as a coolant to obtain solid particulate melamine having a particle size $D_{90}$ of between 10 μm to 1000 μm.

18. Process according to claim 17, wherein the one of the first and second melamine-containing flows used as a coolant in step (d) contains water as a continuous phase.

19. Process according to claim 18, wherein the one of the first and second melamine-containing flows used as a coolant in step (d) which contains water as a continuous phase is the first melamine-containing flow made from a low pressure gas-phase process for the preparation of melamine from urea.

* * * * *